United States Patent
Almanza Vega

(10) Patent No.: US 9,926,504 B2
(45) Date of Patent: Mar. 27, 2018

(54) POWDER MIXTURE OF ABSORBENT FIBRES

(71) Applicant: Maria Carmen Almanza Vega, Puebla (MX)

(72) Inventor: Maria Carmen Almanza Vega, Puebla (MX)

( * ) Notice: Subject to any disclaimer, the term of this patent is extended or adjusted under 35 U.S.C. 154(b) by 0 days.

(21) Appl. No.: 15/300,355

(22) PCT Filed: Mar. 30, 2015

(86) PCT No.: PCT/MX2015/000055
§ 371 (c)(1),
(2) Date: Apr. 6, 2017

(87) PCT Pub. No.: WO2015/152706
PCT Pub. Date: Oct. 8, 2015

(65) Prior Publication Data
US 2017/0204343 A1    Jul. 20, 2017

(51) Int. Cl.
| | | |
|---|---|---|
| *B01J 20/28* | (2006.01) | |
| *C10L 1/02* | (2006.01) | |
| *C07C 29/76* | (2006.01) | |
| *C07C 67/56* | (2006.01) | |
| *B01J 20/22* | (2006.01) | |
| *E02B 15/00* | (2006.01) | |
| *B09C 1/00* | (2006.01) | |

(52) U.S. Cl.
CPC ............ *C10L 1/02* (2013.01); *B01J 20/22* (2013.01); *B01J 20/28023* (2013.01); *B09C 1/002* (2013.01); *C07C 29/76* (2013.01); *C07C 67/56* (2013.01); *E02B 15/00* (2013.01); *C10L 2200/0469* (2013.01); *C10L 2200/0476* (2013.01); *C10L 2290/544* (2013.01)

(58) Field of Classification Search
CPC ....................................................... B01J 20/24
See application file for complete search history.

(56) References Cited

U.S. PATENT DOCUMENTS

| | | | |
|---|---|---|---|
| 4,072,794 A | 2/1978 | Tomita | |
| 4,919,820 A | 4/1990 | Lafay | |
| 4,925,343 A | 5/1990 | Raible | |
| 5,009,790 A * | 4/1991 | Bustamante | C02F 1/281 134/7 |
| 5,186,831 A | 2/1993 | DePetris | |
| 6,391,120 B1 | 5/2002 | Silva | |
| 2012/0111797 A1 | 5/2012 | Lavoie | |

FOREIGN PATENT DOCUMENTS

| | | |
|---|---|---|
| WO | WO9845018 | 10/1998 |
| WO | WO2011036508 | 3/2011 |

* cited by examiner

*Primary Examiner* — Peter F Godenschwager
(74) *Attorney, Agent, or Firm* — Defillo & Associates; Evelyn A Defillo

(57) ABSTRACT

This invention relates to a powder mixture of absorbent fibers with oleophilic and hydrophobic properties, to a process for separating and/or collect oil, petroleum and all kinds of hydrocarbons, solvent or other selected liquid from oil, gasoline, diesel, solvents, antifreezes, acetone, ether, paraffins, waxes or oil paints, or combinations thereof, both in water and earthy soils involves the use of a powder mixture of absorbent fibers and recyclable adsorbents, the method for producing the mixture and their applications.

15 Claims, No Drawings

POWDER MIXTURE OF ABSORBENT FIBRES

TECHNICAL FIELD

The present invention pertains to the technical field of biotechnology. In particular it relates to the processing of contaminated waste generated by the industry of oil refining and/or petrochemical, and more particularly to a process for separating and/or collect oils, oils and all hydrocarbon solvent or other selected liquid between oils, gasoline, diesel, solvents, anti-freeze. ketones, ethers, paraffin, waxes or oil paints, or combinations thereof, both in water and earthy soils involves the use of a powder mixture of absorbent fibers and recyclable adsorbents, the method for producing the mixture, and as their applications.

BACKGROUND

Oil spills, solvents and hazardous materials are an ongoing problem that has serious environmental consequences, including damage to oceans, beaches, rivers and streams, as well as the detrimental effects on the health of wildlife and humans The need for oil and chemicals has created a steady growth in the chemical industry, including transport and manufacture of these compounds, resulting in increasing environmental problems associated with spills, accidents and improper disposal.

The documents listed below describe different solutions to remedy the problems associated with oil spill or other liquid contaminants from soil and water.

Such is the case of U.S. Pat. No. 7,041,221 (B2) patent. which claims a method comprising the use of ground glass to remove oil from the surfaces containing it, which comprises the step of applying the said glass to the surface of the oil contained in it said glass is formed by the process (a) crushing glass using an impact crusher, hammer mill, cone crusher or roll crusher, (b) select crushed glass using at least one mesh, and (c) drying the crushed glass whereby the amount of oil is reduced from the surface.

Another example is described in the international application WO2009001676. It refers to the use of magnetism by a magnetic for treating water contaminated with oil occurs in oil production and reuse the same separator. The magnetic separation system subjected to flocculation by a flocculation magnetic separator to thereby obtain a preliminary purified water free of oil pollution components contained in the oil-contaminated water.

Additional prior art it is known methods involving the use of microorganisms to recover oil. The U.S. Pat. No. 8,357, 526 (B2) and US 20-7776795 (B2) patents relate to the isolation and identification of *Pseudomonas* strains unique stutzen that can grow on crude oil denitrification conditions and which are useful in oil recovery.

Moreover, for many years they were used absorbent materials in cleaning oil and hazardous materials industry. absorbent clay materials are currently the material of choice for the absorption or recovery of oil or other hazardous chemicals in soil. A wide variety of treated natural fibers have been used as adsorbents hazardous materials. These have included tree bark, peat, wood fiber, kenaf core, puffed cereals, and a variety of other cellulosic materials. Each of these types of fibers has drawbacks that have prevented them from becoming the material of choice for oil and chemical spills on land or in water.

The main disadvantage of most of these fiber types is that they are naturally hydrophytes and, therefore, tend to absorb large amounts of water The water absorption increases the weight of these materials and may decrease healthily their ability to absorb oil or hazardous chemical that these materials are intended to recover.

In industrial applications, these materials have the disadvantages of low absorption capacity and a high density that make both heavy and difficult to transport them. In addition, the abrasiveness and friability of these products can lead to increased wear of the nearby industrial machinery. Some of these adsorbents are not biodegradable and. therefore, pose an additional environmental problem, as they must be eliminated in the limited space available in landfills.

The international patent application WO2011036508 A1 describes a process for recovering hydrocarbons, to decontaminate water and soil, especially aimed at maintaining clean environment, and allowing the industry generally achieve adequate waste management and as methods for water treatment, quick, cost-effective, efficient manner unlike known technologies. However, in this application not using a mixture of absorbent fibers powder for this purpose is described.

Therefore, a need exists for an efficient naturally absorbent material is environmentally friendly and overcomes the drawbacks of known technologies in the prior art.

BRIEF DESCRIPTION OF THE INVENTION

The present invention provides a powder mixture of absorbent fibers being biodegradable after use and recovered hydrocarbons, solvent or other liquids easily, such as oils, gasoline, diesel, solvents, antifreeze, acetone, ether, paraffin, waxes or paintings oil.

It is therefore a first object of protection a powder mixture of absorbent fibers oil, solvent or other liquids on any surface that contains the absorbent mixture comprises among its ingredients: a) *Typha latifolia*: b) *Enhorna crassipas* (Jacinto); *Opontia mucilage* FIEOS (cactus (nopal)); c) *Sorghum bicolor* L 'd) *Avena sativa* (cereal straw); e) *Solalum melongena* (eggplant); f) *Tribcum aestivum* (bran husk tngo); g) *Cocos nucifera* (coconut fiber), h) *Schizolobium parahyba*. i) *Heliopsis tongtpes* (root chllcuaje); *Yucca elephantipes* (Izote).

A second object of protection refers to a method for absorbing oil, solvent or other liquids on any surface that contains them.

A third object of protection refers to the bedspreads and sheets made of woven wrapper to absorb hydrocarbons, solvents or other liquids on any surface that contains fibers.

A fourth object of protection relates to a method for producing a biomass fuel comprising the steps a) adding a mixture of absorbent fibers powder on a surface containing oil or other liquid solvent; and b) pressing the powder mixture of fibers to extract oil, solvent or other liquid.

The objectives of the present invention aforementioned and still others not mentioned will be apparent from the description of the invention and the figures with an illustrative and non-limiting accompanying which are presented below.

DETAILED DESCRIPTION OF THE INVENTION

Today herbaceous plants and *Eichornia crassipes Tyfha latifolia*, among a variety of other tropical plants are considered as waste agricultural by-products in the countries in which they occur. Currently, these products are disposed of in landfills, where they can attract insects and contribute to landfill capacity problems. Furthermore, they can be discarded into rivers where they are oxidized and can cause environmental problems potential.

In other cases, the products are left on the floor to act as a natural fertilizer.

The advantageous effects of the powder mixture of absorbent fibers, is that this is a product that can be produced all year since different parts of Mexico. such as the state of Tabasco is available, particularly among swamps. In order to not affect the environment, the plants used to produce the powder mixture are cut with rationality, and in this way also helps to solve the problems of aquifers, such as permanent water logging and cutting the nests dengue carrier mosquito. In addition, jobs are created in areas devastated by fires out of control wells. In addition to savings for Mexico not to bring distant to absorb oil or other liquid products.

Another of the advantages of the invention described is that there is enough material in the marshland of the state of Tabasco and a thicket that makes plague of insects as the carrier dengue mosquito swoops to cut their nests as they proliferate throughout the area is a source of contamination by flooding rainwater without being rainy weather remains the ecological imbalance in the Gulf of Mexico material is needed for cleaning the literal and costs are lower than the ones produced in other regions of America. In addition, there is a constant need for products capable of absorbing polluting materials in soil, rivers, lakes and the sea, without otherwise affecting the environment.

The powder made of marsh plants for their years of life are wastes and residues of legumes and natural polymers cactus mucilage make this powder is a great absorbent oil and chemicals for cleaning rivers lakes and sea, as well as earthy soil of a large absorbent chemical materials for use in Gas by dump gasoline and diesel.

The powder mixture of absorbent fibers oil, solvent, and other liquids on a surface that contains, among its ingredients comprises:
a) *Typha latifolia* (aerial part);
b) *Eichornia crassipes* (Jacinto, water lily);
c) *Sorghum bicolor* L. (aerial part);
d) *Avena sativa* (cereal straw);
e) *Solalum melongena* (eggplant);
f) *Triticum aestivum* (wheat bran husk);
g) *Schizolobium parahyba*; (dry leaves);
h) *Yucca elephantipes* (Izote, leaves)

The present invention provides the possibility of incorporating conservative selected from calcium propionate, sodium benzoate and ammonium propionate, or combinations thereof.

One conservative as used in the present invention is an aqueous solution obtained from *Heliopsis longipes* (root chilcuaje). Which is obtained by placing 500 gr. Root *Heliopsis longipes* in a container with 15 liters of boiling water for about 20 to 40 min. Preferably 30 min.

During the process of preparing the powder mixture can be added binders, preferably a mixture of mucilage of *Opuntia ficus* and an aqueous solution of seed *Linum usitatissimum* (linseed). This mixture is made as follows: To prepare the mucilage of *Opuntia ficus* used approximately 3 kg. nopal diced, put in boiling water for 30 min, the liquid comprising the mucilage is separated. Furthermore, 3 kg are used. *Linum usitatissimum* seed (linseed), which are placed in boiling water for 30 min. They slip and used only the liquid, which is mixed with the liquid comprising the nopal mucilage The present invention contemplates the use of materials to reduce or eliminate the tendency of some of absorbing water by treatment with chemical additives to increase their hydrophobicity, using finely ground cellulose treated with a hydrophobic agent such as paraffin, other waxes, alcohol polyvinyl, hydroxyethyl cellulose or similar. These additives are added during manufacture of the powder mixture of absorbent fibers.

Additionally, you can use dyes that are added to the powder mixture at the end of processing, within which highlights the natural colors, but preferably fibers *Cocos nucifera*, which is purchased in presentations bags 250 g is used.

Method for Manufacturing the Powder Blend of Absorbent Fibers:
a) The method for manufacturing the powder blend of absorbent fibers begins with the cutting and selection of parts of plants selected *Typha latifolia* (aerial part); *Eichornia crassipes* (aerial part); *Sorghum bicolor* L (grain); *Avena sativa* (stem); *Solalum melongena* (fruit); *Triticum aestivum* (wheat bran husk); *Schizolobium parahyba* (leaves); and *Yucca elephantipes* (leaves); which are brought to the workshop for runoff separately;
b) Each of the plants and/or plant parts separately washed with sodium hypochlorite at 0.5% dilution with water pressure to remove dirt;
c) Each of the plants and/or plant parts are placed separately direct the sun to dry at a temperature of 25 to 34 Co, for a time of between 7 to 12 hours, until a preferred moisture between 4% to 9%;
d) Once the desired humidity is obtained and the plants and/or parts thereof are dry, they proceed to perform ground to obtain a powder with particle size of about 0.5 microns, except *Sorghum bicolor* L, which is obtained a flour with particle size of 0.2 microns;
e) The powders obtained in a mixer, in the following percentages are mixed: *Latofia Typha* between 15-25%; *Eichornis crassipes* between 15-25%; *Sorghum bicolor* L. 5-10; *Avena sativa* between 5-10%; e) enters *malangona Solalum* 15-25%; *Trificum aestivum* 5-10%); *Schicolobium parahyba* between 5-10%; and *Yucca elephantipes* between 5-10%.
f) Are impregnated with 20 to 35 liters per 20 kg. dry powder of a mixture of mucilage and aqueous *Opuntia* spp seed *Unum usitatissimum* (linseed);
g) Is put back to dry at a temperature of 25 to 34° C., for a time of between 7 to 12 hrs;
h) Optionally additives such as preservatives and/or dyes are added;
i) It is placed in sacks of 20 kilos, labeled and removed for sale.

Method for Application

The method for absorbing oil, solvent or other liquid comprising the steps of: a) adding a sufficient amount of between 800 g. 1,200 gr. powdered fiber per 2 to 4 liters or space to absorb on a surface containing materials absorb; and b) collecting the mixture of fiber impregnated with the contaminant, either by mechanical or manual. A One kilogram of the powder mixture has the ability to absorb 4.5 liters of crude oil.

For this case, three different products according to the application are manufactured:
1) Bulk: applied directly to clean up spills.
2) Linen or pillows: apply directly on spills and subsequently are compressed to remove the oil or other liquids.

3) Oleophilic cords, although these are of different types on the market, but they are mainly made of synthetic fibers such as polypropylene and do not consider fire-resistant materials, significant differences referred to in this work is that they are made of fireproof fabric and fiber natural, giving advantages in applying oil spill in wells with fire, as often happens.

Once it is worn away the mixture after being recovered used repeatedly, it can be useful in filling potholes adding chapapoto or to assist in the mixture of mud bricks and blocks, their role in these applications is that it serves as a membrane to toughen and material savings, ie acts as a composite.

Oleophilic Cord and Containment Fences

The oleophilic cords and containment fences, demarcate the contaminated areas, to recover the contaminant. They are made of flame retardant fabrics that are filled with the powder mixture of absorbent fibers.

The oleophilic cords (1) are made in a sheath Flame retardant cotton fabric 1 cm thick by 1.56 m long and 0.48 m wide; the sleeve is filled with the powder mixture of absorbent fibers with a modular spoke for coupling various strands, as many as are required in the application. They have hooks (2) (4) stainless steel and a plurality of loops of stainless steel to hold them with ropes and pull them with greater ease in handling. This is also a difference from existing cords, since the latter must be handled by operators in arms. Oleophilic cords with contaminated water as both earthy soil area is delimited, these cords are impregnated or absorb hydrocarbon and then placed in a press and squeezed to remove and recover both materials. The recovered oil is analyzed in the laboratory to ensure proper management and use; the oleophilic cords are reused many times permitted wear and finally can be used in filling potholes or manufacture of adobes.

The oleophilic cords presented in this application to be made of natural fibers, ensuring advantages of biodegradability, atoxicity and 20 with respect to recycling existing.

Method for Producing Fuel

The method for producing biomass fuel 25 comprises the steps a) adding a mixture of absorbent fibers powder on a surface containing oil or other liquid solvent; and b) pressing the powder mixture of fibers to extract oil, solvent or other liquid, c) moving the impregnated fiber to laboratory for separation of the contaminant and to reuse both the fiber and the chemical.

Uses

The powder mixture of absorbent fibers can be used in chemical manufacturing company's oilers as perfumes, candles factories, carters to delineate the contamination spread on the ground, also to absorb traces blood and other fluids. And to absorb odors.

Diapers and towels are made with cotton blanket, a natural fiber so slow to degrade three months while conventional items take up to 20 years.

Pillows and mattresses in hospitals, especially in infectious diseases rooms where the death of the patient, they must be discarded not generating, contamination of a conventional mattress or pillow.

Moreover, once this out of the sea poured into hydra lime and tar as it makes a membrane and strengthens the materials, it is used to fill the potholes on the roads and paths.

BEST METHOD FOR CARRYING OUT THE INVENTION

This example is illustrative and not limiting since one skilled in the art will understand that there are variations that fall within the scope of protection of the present invention.

Powder Mix of Absorbent Fibers and Method for Manufacturing a) Cut and select parts of the following plants: *Typha latifolia* (aerial part), *Echomia crassipes* (aerial part); *Sorghum bicolor* L (grain). *Avena sativa* (stem); *Solaium melongena* (fruit); *Triticum estivum* (bran wheat straw), *Schizoloblum parahyba* (leaves); and and *Yucca elephantipes* (leaves); which are brought to the workshop for runoff separately;

b) Wash separately each of the plants and or parts with sodium hypochlorite at a dilution of 0.5% and pressurized water to remove dirt;

c) Drying the sun each of the plants and/or plant parts separately at a temperature of 25 to 34 C ° for a time of between 7 to 12 hrs., until a preferred moisture from 4 to 9%;

d) Grinding the plants and/or parts thereof to a powder with particle size of about 0.5 microns, except *Sorghum bicolor* L, which flour with grain size 0.2 micron is obtained;

e) Mix the powders obtained in the following percentages: *Typha latjfolia* 20%; *Crassipes Eichornia* 20%; *Sorghum bicolor* L 6%; d) *Avena sativa* 6%: e) *Sotalum melongena* 20%; f) *Triticum aestivum* 6%; h) *Schizolobium parahyba* 6%; and *Yucca elephantipes* 5%;

f) Impregnating with 30 liters per 20 kg of dry powder of a mixture of *Opuntia* spp mucilage and aqueous seeds *Linum usitatissimum* (linseed);

g) Drying at a temperature of 25 to 34 Co, for a time of about 8 hours;

h) Add 540, preferably 6% *Cocus nucifera* powder as a colorant;

i) Impregnating with 15 liters per 20 kg of an aqueous solution *Heliopsis longipes* root as conservative;

j) Add 10 to 15% of sodium benzoate and/or calcium propionate as conservative.

k) Pack into containers or bags of 20 Kgs. for labeling.

Example

The development of the present invention is based on tests done at the Polytechnic University of the Gulf of Mexico and the Polytechnic University of Puebla and certification of the Mexican Petroleum Institute and certifying companies Boreau Veritas and Interseco and the qualitative and quantitative analysis Laboratory Federal Electricity Commission (CFE) Lapem Irapuato Gto.

This study consisted of service functionality to a sample 15 of the powder mixture of absorbent fibers by the Mexican Petroleum Institute by test method ASTM F 716-09. In this study the efficiency of absorption in three evidence (diesel, gasoline and crude oil) was determined in the sample called SET-M8.

During the development was carried out the analysis to the sample with light brown color characteristics and classification of type II loose materials.

The results were:

| Absorbing Powder Fibres. [SET-M8] | | | | |
|---|---|---|---|---|
| DETERMINATION | UNITY | MÉTHOD | MEANS TEST | RESULTS |
| ABSORPTION EFFICIENCY | % | ASTM F-716-09 Subsección 11.2 | DIESEL GASOLINE CRUDE OIL | 67.30 60.78 71.73 |

According to the results issued by the laboratory of IMP to sample the powder mixture of absorbent fibers it concluded that exhibits improved efficiency of absorption in the middle of crude oil, MAYA Oil.

Next, there is a list of some liquid absorbing powder mixture of the present invention:

| | |
|---|---|
| CRUDE OIL | ETHYL ETHER |
| ETHYLENE GLYCOL | FUEL OIL |
| ASPHALT BASE OIL (LIQUID) | AMMONIA |
| METHANOL | PHENOL |
| OIL FIELD | BENZENE |
| PENTANE | CORN OIL |
| GASOLINE | SODIUM BENZOATE |
| PESTICIDES | SILICON OIL |
| GLYCERIN | BUTANOL |
| PROPANOL | CUTTING OILS |
| HEPTANE | CHLOROFORM |
| DIESEL | MOTOR OILS INKS |
| MINERAL OILS | HEXANE |
| DIETHANOLAMINE | TURBOSINE |
| PARAFFINIC OILS | ANSECTICIDES |
| ETHANOL | UREA |
| ISOPROPANOL | VEGETABLE OILS |
| | PETROLEUM ETHER |
| | ACETONE |

Then a list of some liquids shown arranged on earth absorbing powder mixture of the present invention:

| | |
|---|---|
| CRUDE OIL BASE | CUT OILS |
| OILS OF ASPHALT | MOTOR OIL |
| OR PARAFFINIC | PARAFFINIC OILS |
| GLICERIN | FUEL OILS |
| MINERAL OILS | VEGETABLE OILS |
| DIESEL | |

The powder mixture of absorbent fibers presents the following technical characteristics:

| PROXIMATE COMPOSITION OF THE PRODUCT: | | | |
|---|---|---|---|
| Carbohydrates (ELN) | 48.9% | CRUDE FIBER | 99% |
| PROTEÍN | | | |
| CRUDE FAT | 7.0% | INORGÁNIC MATTER | 21.6% |
| ORGÁNIC MATERIAL | 1.3% | HUMIDITY | 12.5% |
| IRON | 100% | DRY | 99% |
| | 40% | LANDS | 40% |

| RISK INDEX: | | | |
|---|---|---|---|
| MÍNIMUM = 0 LIGHT = 0 MODERATE = 2 HIGH = 3 EXTREME = 4 | | | |
| HEALTH | 0 | TOXICITY | 0 |
| INFLAMMABILITY | 1 | CORROSIVITY | 0 |
| REACTIVITY | 0 | EXPLOSIVE | 0 |

| PHYSICAL DATA PRODUCT: | |
|---|---|
| BOILING POINT: | SOLID NOT APPLICABLE |
| VAPOR PRESSURE: | NEGLIGIBLE |
| WATER SOLUBILITY: | INSOLUBLE |
| APPEARANCE: | PARTICLE 2 to 3 centimeters |
| COLOR: | OCRE TAN AND GREEN PLANT DRY CHARACTERISTIC |
| ODOR: | |
| PH: | 6 to 8 per gallon HYDROCARBON |

| PHYSICAL DATA PRODUCT: | |
|---|---|
| ABSORPTION CAPACITY: | It collect required one kilogram of |
| RETENTION CAPACITY: | Permanent 90 to 99% depending on the specific gravity and nature of hydrocarbon oils and blood or urea. |

| INFORMATIÓN HEALTH RISK: | |
|---|---|
| INHALATIÓN: | NO KNOWN RISK TO WORK THE PRECAUTIONS TO TAKE COVER WITH TRANSPARENT LENSES, AND USE GLOVES HARD COVERS MOUTHS DO NOT PUT WATER NEAR THE TEAM. |
| INGESTIÓN: | NO KNOWN RISK IF ANY DISCOMFORT CONSULT PHYSICIAN. |
| EYES: | MAY CAUSE MILD IRRITATION HIGH CONCENTRATIONS RECOMMENDED INDUSTRIAL USE SAFETY GLASSES |
| SKIN: | NO KNOWN RISK |

| RISK OF FIRE OR EXPLOSION: | |
|---|---|
| AUTOIGNITION TEMPERATURE: | OVER 250 DEGREES POINT BOILING, SOLID, NOT APPLICABLE. |
| FIRE ACCIENTAL ALMANZA PRODUCT: ACCIDENTAL FIRE FORMED BY THE AGLOMERADO ALMANZA and the hydrocarbon and/or oils. | APPLYING ANY AGENT EXTINGUISHER EXTINGUISHING AGENT APPLY, UNDER HIDOCARBURO AND/OR OIL ABSORBED. |

| REACTIVITY. | |
|---|---|
| POLYMERIZATION RISKS: | DOES NOT OCCUR |
| ESTABILITY: | STABLE |
| HAZARDOUS DECOMPOSITIÓN: | NONE KNOWN. |
| MATERIALS TO AVOID: | ANY |
| STORAGE: | DRIED PLACES |

| TOXICITY. | |
|---|---|
| RISKS OF DUST: FORMED HYDROCARBON AGLOMERADO TOXICITY AND/OR OILS; | NOT TOXIC ACCORDING TO THE PROVISIONS DISPOSE ESTABLISHING THE AUTHORITY. |

| PERSONAL PROTECTION | |
|---|---|
| RESPIRATORY TRACT: | FACE MASKS |
| EYES: | INDUSTRIAL SAFETY GLASSES |
| SKIN: | FOR IMPLEMENTATION OF "NOT REQUIRED |

The cords were Oleophilics Certificates with Standard AATCC20/20A issued by the certifying company BERUEAU VERITAS.

| CHARACTERÍSTICS | MÉTHOD | | UNITY | SPECIFICATIÓN |
|---|---|---|---|---|
| Composition | NMX-A-084 | | % | 100% cotton |
| Type ligament | Visual | | | basket |
| width | NMX-A-052 | | Cm | 175 +/− 1 |
| Mass/área | NMX-A-072 | | g/m3 | 407 +/− 5% |
| | | Warp | Threads/cm | 98 +/− 3 |
| Tissue Density | NMX-A-057 | Plot | Threads/cm | 52 +/− 2 |
| | | Warp | Newton | Min. 700 |
| Tensile Strength | NMX-A-059/2 | Plot | Newton | Min 425 |
| | | Warp | % | +/−5% |
| Dimensional change | NMX-A-158 | Plot | % | +/−5% |
| | | Change | Levels of grayscale | Min. 4 |
| Color fastness to washing | NMX-A-074 | Transfer | Levels of grayscale | Min. 4 |
| Perspiratión color fastness | NMX-A-065 | Add | Levels of arayscale | Min. 4 |
| | | Alkaline | Levels of grayscale | Min. 4 |
| Colorfastness to rubbing | NMX-A-073 | Dry | Levels of grayscale | 3-4 |
| | | Damp | Levels of grayscale | Min. 3 |
| Flame resistance after 100 washes | ASTM D-6413 | | Inches | 4 |
| Permanence of the flame | | | Seconds | 2 |
| Heat resistance | NFPA-1975 Sec. 8.2 | | | It does not melt, drip and does not separate, non-combustion |

Alternative Advantages of the Invention are:
I. Silt removal swamp of sewage, with this CO2 emissions, resulting from the decomposition of organic matter in the aquifers will decrease.
II. Natural resources sparingly prey, and the economy is set to relist the mixture for use in different industry sectors within which include cleaning products, candles, perfumes, paints. among others.
III. Nests of dengue disease carrier mosquitos are removed.
IV. Jobs are created in areas with high marginalization.
V. Natural products widely produced in the country and easily accessible are used. lowering import costs.
VI. Pollution (Oil comes is recollected to be sent to the laboratory) is removed in the communities near Oil Wells Drillings.

Although the above description was made taking into account, preferred embodiments of the invention, it should be noted by those skilled in the art, that any changes in form and detail will be within the spirit and scope of the present invention. The terms in which this memory has been drafted, should be understood in a wide and non-limiting sense. The materials. form and a description of the elements. They may vary as long as this does not alter the essential characteristic of the model.

The invention claimed is:
1. A powder mixture of absorbent fibers to absorb oil, solvent or other liquid comprising:
   typha latifolia;
   eichornia crassipes;
   sorghum bicolor L;
   oatmeal sativa;
   solanum melongena;
   triricum aestivum;
   schizolobium parahyba; and
   yucca elephantipes.
2. The powder mixture of absorbent fibers according to claim 1, wherein the fibers are present in the following percentages:
   typha latifolia; between 15-25%;
   eichornia crassipes; between 15-25%;
   sorghum bicolor L; between 15-25%;
   oatmeal sativa; 5-10%;
   solanum melongena; between 15-25%;
   triricum aestivum; 5-10%;
   schizolobium parahyba; 5-10%; and
   yucca elephantipes; 5-10%.
3. The powder mixture of absorbent fibers according to claim 1, further including a binder containing a mixture of *Opuntia* spp mucilage and aqueous solution of *Linum usitatissimum* seeds.
4. The powder mixture of absorbent fibers according to claim 1, further comprising a conservative selected from calcium propionate, sodium benzoate, ammonium propionate, or combinations thereof.
5. The powder mixture of absorbent fibers according to claim 4, further comprising as an additional conservative an aqueous solution from *Heliopsis longipes* root.
6. The powder mixture of absorbent fibers according to claim 1, further comprising materials to reduce or eliminate the tendency of some of absorbing water by treatment with chemical additives to increase their hydrophobicity, selected from the group consisting of paraffin, waxes, polyvinyl alcohol, hydroxyethyl cellulose, and combinations thereof.
7. The powder mixture of absorbent fibers according to claim 1, further comprising dyes selected from natural dyes, artificial dyes, or combinations thereof.
8. The powder mixture of absorbent fibers according to claim 7, wherein the dye is *Cocos nucifera* powder.
9. The powder mixture of absorbent fibers according to claim 1, wherein the oil or the other liquid is selected from at least one of the following: crude oil, residual fuel oil, asphalt base oil, phenol, canola oil, corn oil, gasoline, silicone oil, glycerine, cutting oils, heptane, motor oils, hexane, mineral oils, insecticides, paraffinic oils, vegetable oils, isopropanol, acetone, ethyl ether, ethylene glycol, ammonia, methanol, benzene, pentane, benzonato sodium, pesticides, butanol, propanol, chloroform, inks, diesel, jet fuel, diethanolamine, urea, ethanol, petroleum ether, or combinations thereof.
10. The powder mixture of absorbent fibers according to claim 1, wherein the oil is selected from at least one of the following: crude oil asphaltic base, paraffinic mineral oils, paraffinic oils, fuel oil, vegetable oils, diesel oils, cutting, glycerine, motor, or combinations thereof.
11. A method for absorbing oil, solvent or other liquid, comprising the steps of: adding between 800-1200 gr of mixture of absorbent fibers powder of claim 1 to surface containing the oil, solvent, or other liquid.

12. A cord to absorb oil, solvent, or other liquid, comprising inside a powder mixture of absorbent fibers as claimed in claim 1.

13. The cord according to claim 12, wherein the cord is made of fireproof fabric and cotton fibers.

14. The cord according to claim 12, wherein different laces are coupled to define a contaminated water in earthy soil area.

15. A method for the production of biomass fuel comprising adding the powder mixture according to claim 1 over a surface containing oil and pressing the powder mixture according to claim 1 to extract the oil.

\* \* \* \* \*